United States Patent [19]
Kosaka et al.

[11] Patent Number: 5,521,699
[45] Date of Patent: May 28, 1996

[54] IMAGING FLOW CYTOMETER AND IMAGING METHOD HAVING PLURAL OPTICAL PATHS OF DIFFERENT MAGNIFICATION POWER

[75] Inventors: Tokihiro Kosaka, Kakogawa; Shinichi Ogino, Kobe, both of Japan

[73] Assignee: TOA Medical Electronics Co., Ltd., Japan

[21] Appl. No.: 280,816

[22] Filed: Jul. 26, 1994

[30] Foreign Application Priority Data

Jul. 26, 1993 [JP] Japan .................................... 5-183973

[51] Int. Cl.[6] .................................................. G01N 15/14
[52] U.S. Cl. ............................................. 356/73; 356/39
[58] Field of Search ................................. 356/23, 73, 39

[56] References Cited

U.S. PATENT DOCUMENTS

| 4,522,475 | 6/1985 | Ganson ................................ 356/23 X |
| 5,159,397 | 10/1992 | Kosaka et al. ....................... 356/23 X |

FOREIGN PATENT DOCUMENTS

| 63-94156 | 4/1988 | Japan . |
| 3-105235 | 5/1991 | Japan . |
| 3-52573 | 8/1991 | Japan . |
| 4-72544 | 3/1992 | Japan . |
| 4-72545 | 3/1992 | Japan . |
| 5-79970 | 3/1993 | Japan . |
| 5-79971 | 3/1993 | Japan . |

*Primary Examiner*—Vincent P. McGraw

[57] ABSTRACT

An imaging flow cytometer includes a flow path such as a transparent tube for allowing subject particles to move in a separate fluidity, the subject particles being present in a sample liquid, a light source for applying light to the subject particles which flow through the transparent tube, a beam splitter for distributing to two optical paths image light obtained from each of the subject particles irradiated with the light, a capturing device which has a light receiving surface on which an image is formed, projectors for magnifying at different magnification powers each image light distributed by the beam splitter and forming an image on respective portions of the light receiving surfaces of the capturing device, and an image processor for storing and displaying images of particles captured by the capturing device.

23 Claims, 8 Drawing Sheets

FIG. 5
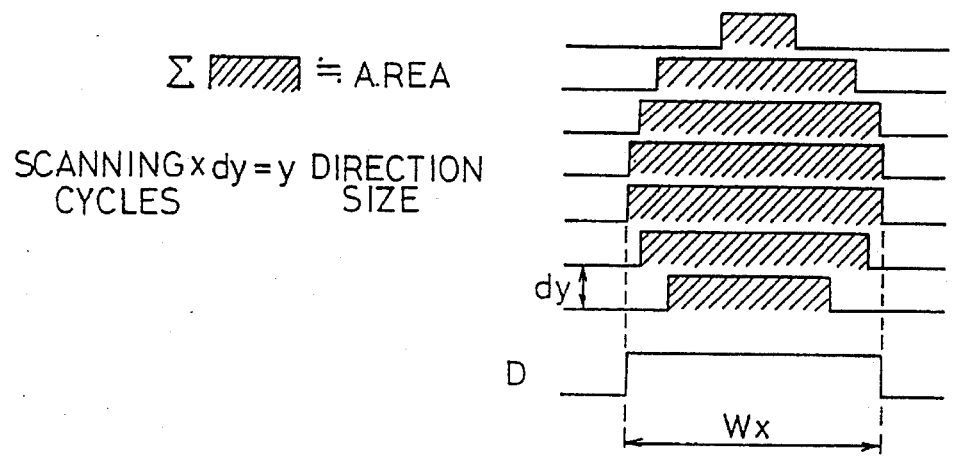
FIG.6(a)        FIG.6(b)
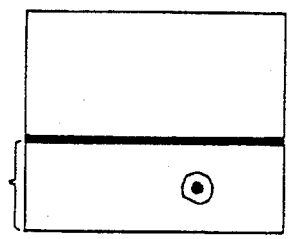   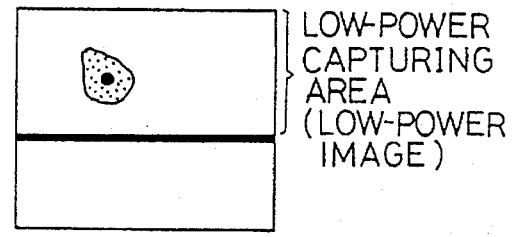

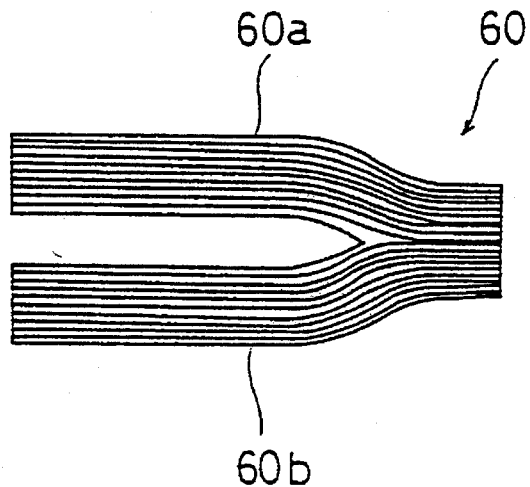
FIG. 9A  FIG. 9B
FIG. 10
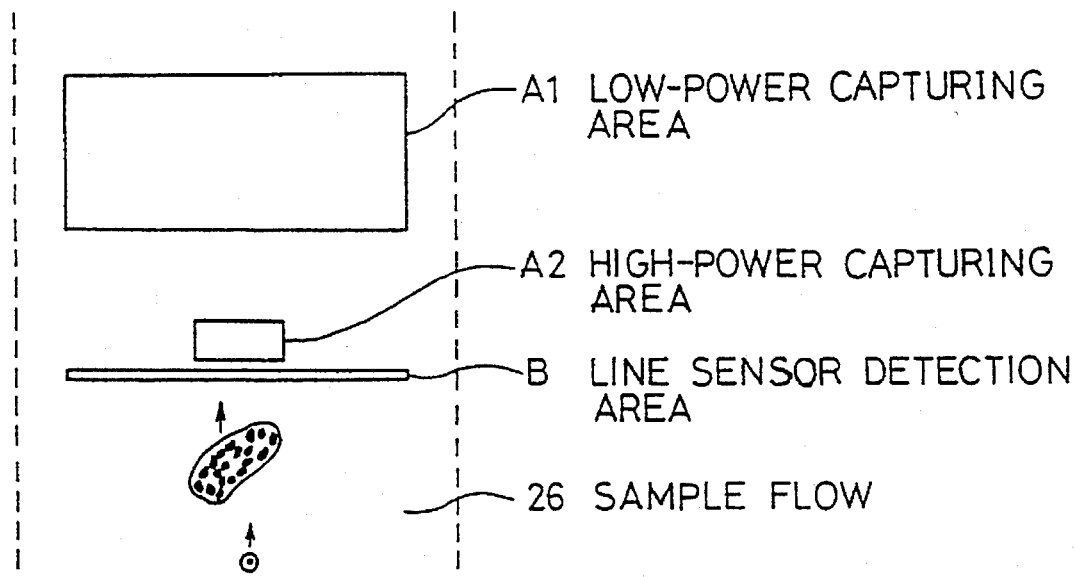
- A1 LOW-POWER CAPTURING AREA
- A2 HIGH-POWER CAPTURING AREA
- B LINE SENSOR DETECTION AREA
- 26 SAMPLE FLOW

IMAGING FLOW CYTOMETER AND IMAGING METHOD HAVING PLURAL OPTICAL PATHS OF DIFFERENT MAGNIFICATION POWER

BACKGROUND OF THE INVENTION

1. Field of the Invention

The present invention relates to a flow cytometer for investigating particle constituents that flow in liquids, and more particularly to an imaging flow cytometer for capturing with a video camera particles, such as blood cells in blood or cells in urine, by allowing a sample liquid prepared by diluting blood or urine specimen to pass through a transparent tube called a flow cell.

2. Description of the Background Art

In accordance with a conventional method, a sample liquid, such as blood and urine, in which cells are flowing is introduced into a flow cell having a flat cross section so that images of cells that pass through the flow cell are captured with a system combining a flash lamp and a video camera. Apparatuses for investigating urinary sediment constituents have already been developed which incorporate such an image capturing system.

Subject cells in urinary sediment range from germs and erythrocytes having a size of several μm to epithelium and casts having a size of several hundred μm. In microscopic investigation, the range of vision (magnification) is set to two magnification levels; a high-power field(HPF) and a low-power field(LPF).

FIG. 12 is a view illustrating the outline of a conventional imaging flow cytometer.

In FIG. 12, Reference Numeral 24 designates a flow cell, 26 a sample flow that flows in the flow cell 24, 10 a flash lamp for irradiating the flow cell 24 with light, 12 a collimator lens for rendering parallel the light coming from the flash lamp 10, 20 an iris for restricting the light, 22 a condenser lens for converging the parallel light, 28 an object lens and 54 a lens switching device. The lens switching device 54 is capable of switching between a x4 relay lens and a x1 relay lens. Reference Numeral 50 designates a video camera for capturing an image of particles in the sample flow 26, 56 an image processor for processing a particle image captured by the video camera 50.

In this manner, conventional imaging flow cytometers are provided with a plurality of magnifying relay lenses, which are physically switched to magnify particles with a desired magnification.

However, when imaging flow cytometers of these kinds magnify the power of photography in a sequence of capturing small particles, the result is that large particles are left undetected. On the contrary, when the imaging cytometers reduce the power of photography in a sequence of capturing large particles, small particles are left undetected. Thus, when small particles and large particles consecutively flow through the flow cell, the imaging flow cytometers cannot switch the magnification of the lens immediately. Therefore, such cytometers obtain only images that can be captured with the selected magnification. In other words, either the large or the small particles are left undetected in any event.

In addition, since the flash lamp 10 is flashed at equal intervals of one-thirtieth second in conformity with the frame cycle of the video camera 50 regardless of whether or not particles pass through the capturing region of the video camera 50, the imaging flow cytometers obtain many images free of the particles during examination of samples containing a small amount of particle constituents like urine. In other words, the imaging flow cytometers cannot photograph cells that pass through the flow cell 24 with certitude.

As described above, when samples contain particles having various sizes and the particle concentration is low, such as with urine, the conventional imaging flow cytometer, which can analyze only a small amount of samples as a practical matter, has a drawback of being likely to ignore clinically important cells.

The present invention has been made in view of the above, and the invention provides an imaging flow cytometer that can immediately switch the magnification of lenses depending on the size of particles even if subject samples (like urine) contain particles having different sizes ranging from several μm to several hundred μm. Thus such imaging flow cytometer is capable of efficiently capturing both large and small particles while switching the magnification.

The following apparatus are known which capture particle constituents in a sample liquid by allowing the sample liquid to flow through a flow cell.

At the outset, as described in Japanese Patent Publication No. HEI 3-52573, an apparatus is known which applies a strobe light to a flow of a sample liquid that flows through a flat flow cell to capture static images of particle constituents with a video camera and processes the images.

Furthermore, as described in Japanese Published Unexamined Patent Application No. SHO 63-94156, an apparatus is known which comprises an optical system for capturing a particle image downstream of an optical system which triggers the photographic system in which static images of cells are captured with the system for capturing the particle image after the cells are detected with the optical system trigger.

Still furthermore, as described in Japanese Published Unexamined Patent Application No. HEI 4-72544 and Japanese Published Unexamined Patent Application No. HEI 4-72545, an apparatus is known which comprises an optical system for detecting a particle and an optical system for capturing the particle; in which a particle detecting area and a particle capturing area are formed so that the particle detecting area traverses the particle capturing area, thereby enabling capturing of particle images as soon as particles enter the particle detecting area.

On the other hand, as described in Japanese Published Unexamined Patent Application No. HEI 3-105235, an apparatus is known which captures static images of particle constituents having different sizes by switching the magnification of the lens during the measurement of particles.

SUMMARY OF THE INVENTION

The present invention provides an imaging flow cytometer including:
- a flow element having a transparent passage through which subject particles move in a separate fluidity, the subject particles being present in a sample liquid;
- an irradiator for irradiating with light a sample liquid flow which flows in the transparent passage;
- a beam splitter for distributing to at least two optical paths light from each of the particles that are present in the sample liquid flow irradiated with the light;
- a capturing element which has a light receiving surface on which an image is formed;

a projector for magnifying at different magnification powers each light distributed by the beam splitter and forming an image on respective portions of the light receiving surface of the capturing elements; and an image processor for storing and displaying images of particles captured by the capturing element.

The imaging flow cytometer of the present invention splits into at least two portions (optical paths) the image light obtained from the subject particles and then magnifies at different magnifications each portion of the subject particle images to form an image on the light receiving surface of the capturing element. Thus, such imaging flow cytometer can easily obtain the image of the subject particle corresponding to the magnification of each lens, thereby eliminating a mechanical operation of lens magnification switching.

From a different viewpoint, the imaging flow cytometer of the present invention further includes:

an auxiliary irradiator for irradiating with light the sample liquid flow at a location upstream of the area irradiated by the irradiator;

a particle detector for detecting the size of particles that are present in the sample liquid flow by detecting the light from the particle irradiated by the auxiliary irradiator; and a controller for irradiating the sample liquid flow by the irradiator when the detected subject particle reaches the capturing area corresponding to the size of the detected subject particles so that an image of each of the detected subject particles is captured at the magnification power corresponding to the size of the detected subject particles.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be described in detail in conjunction with the accompanying drawings, which are given by way of illustration only and thus are not intended to limit the scope of the present invention, wherein:

FIG. 5 is a view showing an example of the processing of an output signal from a line sensor camera.

FIGS. 6(a) and 6(b) are views of a capturing screen.

FIG. 9 is a view showing a structure of a light flash-fiber bundle.

FIG. 10 is a view showing a capturing area of a sample liquid in another embodiment.

DESCRIPTION OF THE PREFERRED EMBODIMENTS

Figure 1:
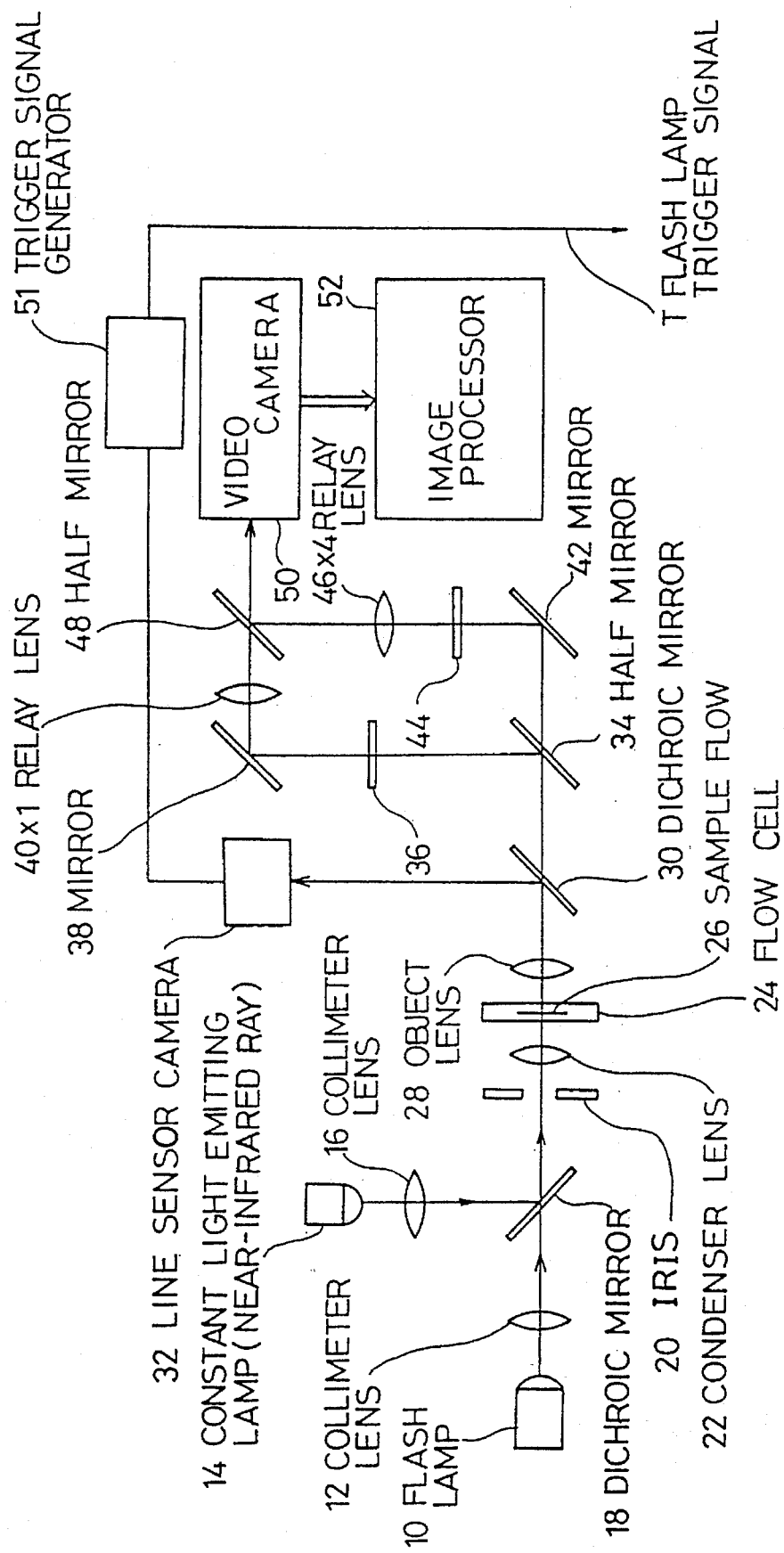
FIG. 1 is a view showing an imaging flow cytometer according to one embodiment of the present invention.

As a flow element of the present invention, any kind of device can be used which provides a transparent passage into which a sample liquid containing subject particles is introduced to allow the subject particles to move in a separate fluidity.

A sample liquid that can be introduced into the tube may be any liquid that contains the subject particles. The sample liquid in which blood and urine are arbitrarily diluted can be applied. Sea water, lake water and river water can be used as the sample liquid depending upon the usage.

As a transparent passage, a flat transparent tube called a flow cell is adopted. In order to clearly capture subject particles contained in the sample liquid, a known flow cell can be used which can form a flat sample liquid flow having a width of about 50 μm to 300 μm and a thickness of about one tenth thereof so that subject particles are separated and flat particles can be oriented toward the front with respect to the direction of capturing and can be moved in a fluidity. For example, a flow cell described in Japanese Published Unexamined Patent Application No. HEI 3-105235 can be referred to.

The light-transmittance rate of this tube may be such that it allows capturing from the outside thereof subject particles that flow therethrough. The tube may be made of glass, plastics or synthetic resin having the light-transmittance rate equal to that of glass, and plastics.

As an irradiator, a light source can be used which applies a pulse light, for example, a strobe light or a flash light to an object at an arbitrary timing. The pulse light application period from the irradiator can be set in the following way with respect to a flow rate of the subject particles. When the flow rate of the subject particles is set to v[m/s] and the pulse light application time is set to t[μs], the shift U in the image of subject particles is given as U=vt. Consequently, when the shift U is less than the capture resolution, a favorable static image of subject particles can be obtained. For example, lowering the shift U in the image of the subject particles to 0.3 [μm] or less may require setting the pulse application time to $t \leq 3$ [μs] when an equation of $v=0.1$[m/s]=100[mm/s] is given.

As a beam splitter, any kind of optical element can be used that can distribute to at least two optical paths light from subject particles. For example, a half mirror can be used.

As capturing element, any element may be used as long as the element can capture images of subject particles by forming the images on the light receiving surface when the subject particles are present in the capturing area and the element can output the captured images by converting them into electric signals. For example, a commercially available video camera can be used.

The capturing area is an area formed when the light receiving surface of the capturing element is projected onto the flow region of particles.

As a projector, any element may be used as long as the means can magnify at different magnification powers each light distributed by the beam splitter respectively and can form images thereof on respective portions of the light receiving surface of the capturing element. An optical magnifier may be preferably used. As the optical magnifier, any kind of lens such as a relay lens or the like can be used. Such lens may have an arbitrary power of x1, x1.5, x2 or x4.

As image processor can be used that converts entered image data into digital data to process each kind of image, and outputs the digital data by converting it into analog data.

In the imaging flow cytometer of the present invention, the capturing element may comprise one video camera whose light receiving surface is projected to the transparent passage to form two capturing areas defined on the sample liquid flow. Thus each of the projectors magnifies the subject particles in each capturing area so that images of the subject particles are formed on each portion of the light receiving surfaces.

As a particle detector, any element may be used as long as it can optically detect the size of the subject particles that are present in the sample liquid. Any kind of optical device can be used. A device which may be used is a combination of a constant light-emitting source such as a LD that can emit a near-infrared ray and an image sensor that has a major dimension of a light receiving surface extending in a particular primary direction for detecting the light. In such case, the capturing area of the image sensor preferably formed in such a manner that the area extends along the flowing direction of the subject particles.

The irradiator may be constituted of light sources the number of which is equal to the number of sections of the divided capturing area. In such case, a light guide is preferably provided for applying light from each light source to each section of the divided capturing area respectively so that images of the subject particles at each magnification is formed on each of the divided light receiving surfaces by the light coming from each light source.

As an example, the light guide may comprise a branched optical fiber bundle.

In accordance with the present invention, the image light obtained from the subject particles is split, and images of the subject particles are magnified with different magnifications to form the images on the light receiving surface of the capturing element. Thus, a desired power of magnification can be selected and the images of all of the subject particles can be easily obtained depending on the respective magnifications, thereby eliminating the mechanical lens switching operation as has been used in the prior art.

In addition, when the capturing element comprises one video camera, images of subject particles magnified into different sizes are formed on the split light receiving surfaces of the video camera. In such case the investment cost for only one video camera can be reduced.

When an auxiliary irradiator, particle detector and controller are further provided, the subject particle images are magnified depending on the size of the subject particles that has been detected.

Furthermore, when the irradiator comprises light sources equal in number to the number of the divided capturing areas, and a light guide is further provided, subject particle images magnified at each magnification are formed on each of the divided light receiving surfaces depending on light from each light source. Thus, when subject particles flow continuously which may be captured at different magnifying powers, the imaging flow cytometer of the invention can capture images thereof by applying light to each of such subject particles.

The present invention will be detailed by way of embodiments shown in the accompanying drawings, which do not limit the scope of the present invention.

FIG. 1 is a view showing an imaging flow cytometer according to one embodiment of the present invention.

The imaging flow cytometer of the present invention is an apparatus in which a sample liquid prepared by diluting blood or urine is introduced into a transparent and flat tube called a flow cell to form a transparent and flat sample flow. Such imaging flow cytometer applies a strobe light to the sample liquid so that a video camera incorporated in the cytometer functions to capture particles (which may be called subject particles in particle tests) such as cells contained in the blood or cells contained in the urine followed by displaying the captured images on a display.

In FIG. 1, Reference Numeral 24 designates a flow cell comprising a transparent flat tube made of glass, plastics or the like. When a sample liquid is introduced into the flow cell 24 a sheath liquid is introduced so as to cover the surrounding of the sample liquid with the result that a laminar flow of the sample liquid and the sheath liquid flows through the flow cell 24.

Reference Numeral 26 designates a sample flow that moves in fluidity in the flow cell 24. The width of the flat sample flow 26 in the longitudinal direction ranges about 5 to 300 μm whereas the thickness of the sample flow in the latitudinal direction ranges about 5 to 30 μm. Particles like hemocytes and cells that are present in the sample flow 26 move in fluidity in the flow cell 24.

Reference Numeral 10 designates a flash lamp that irradiates with light the sample flow 26 that moves in fluidity in the flow cell 24, 12 a collimator lens that renders parallel light coming from the flash lamp 10, 14 a constant light-emitting lamp (auxiliary irradiator) that emits near-infrared light, 16 a collimator lens that renders parallel light coming from the constant light-emitting lamp, 18 a dichroic mirror that synthesizes light from the flash lamp 10 and light from the constant light-emitting lamp 14, 20 an iris, 22 a condenser lens for collecting parallel light, 28 an object lens, 30 a dichroic mirror for separating light from the flash lamp 10 and the constant light-emitting lamp 14.

The dichroic mirrors 18 and 30 have a function of either reflecting or transmitting light depending on the wavelength thereof. This function allows either separating or synthesizing light coming from the flash lamp 10 and light coming from the constant light-emitting lamp 14, the light coming from the flash lamp 10 being visible, the light coming from the constant light-emitting lamp 14 being near-infrared rays.

Reference Numeral 28 designates an object lens, 30 a dichroic mirror for separating light from the flash lamp 10 and light from the constant light-emitting lamp 14, 34 a half mirror for splitting into two portions (distributed into two optical paths) an image light obtained from the subject particles to which light is applied, 36 and 44 masks restricting the image light, 38 and 42 mirrors, 40 a x1 relay lens, 46 a x4 relay lens, 48 a half mirror for synthesizing image light of particles split into two portions, 50 a light receiving surface on which particle images are formed, or a video camera having an image forming surface on which CCD is arranged in two dimensions so that the light receiving surface of the video camera is projected on the particle flow region to form a capturing area.

Figure 2A:
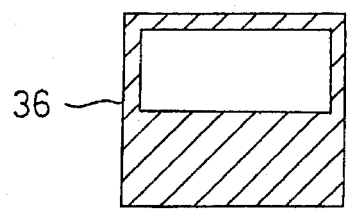
FIGS. 2(a) and 2(b) are views of masks forming part of an embodiment of the invention.
Figure 2B:
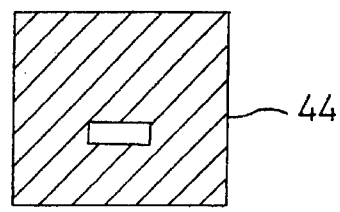

The x1 relay lens 40 and the x4 relay lens 46 magnifies one time and four times, respectively, two images divided by the half mirror 34 and formed on the masks 36 and 44 respectively (FIGS. 2(a) and 2(b)).

The masks 36 and 44 mask areas other than the capturing area of the subject particles corresponding to respective capturing magnifications as shown in FIGS. 2(a) and 2(b). Reference Numeral 52 designates an image processor for taking out subject particle images of subject particles that have been captured with the video camera 50 so that the images are displayed at one time on the CRT display.

Reference Numeral 32 designates a line sensor camera (particle detector) for receiving light coming from a constant light-emitting lamp 14, the light being separated by the dichroic mirror 30 which camera detects the size of the particles in the sample liquid flow 26. Reference Numeral 51 designates a trigger signal generator which generates flash lamp trigger signal T for allowing the flash lamp 10 to emit light every time each of the subject particles reaches a capturing area depending on the selection of whether the particles are to be magnified at the power of 1 or at the power of 4.

In this particular embodiment, the imaging flow cytometer provides a line sensor camera 32 with a primary dimension image sensor and a constant light-emitting lamp 14 for emitting near infrared rays having a wavelength in a region slightly shifted from the visible light region in order to constantly monitor that cells pass through the capturing area of the video camera in the flow cell 24.

Figure 3:
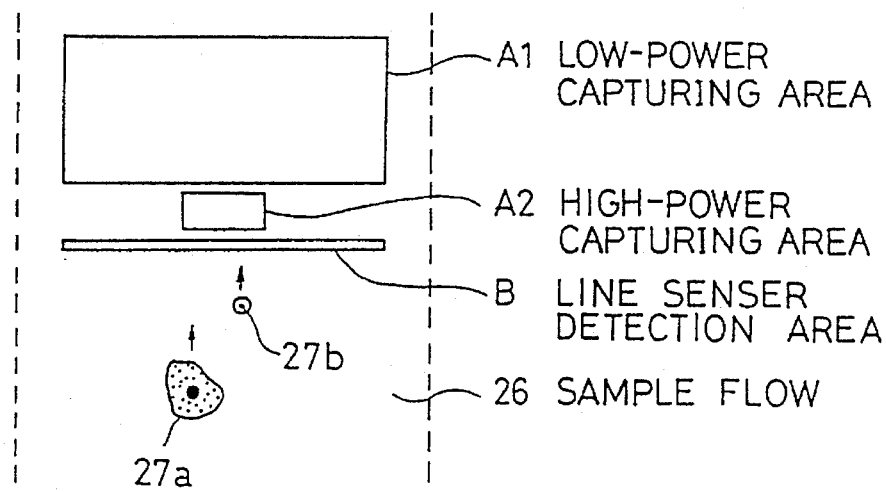
FIG. 3 is a view showing a capturing area of a sample liquid.
Figure 4:
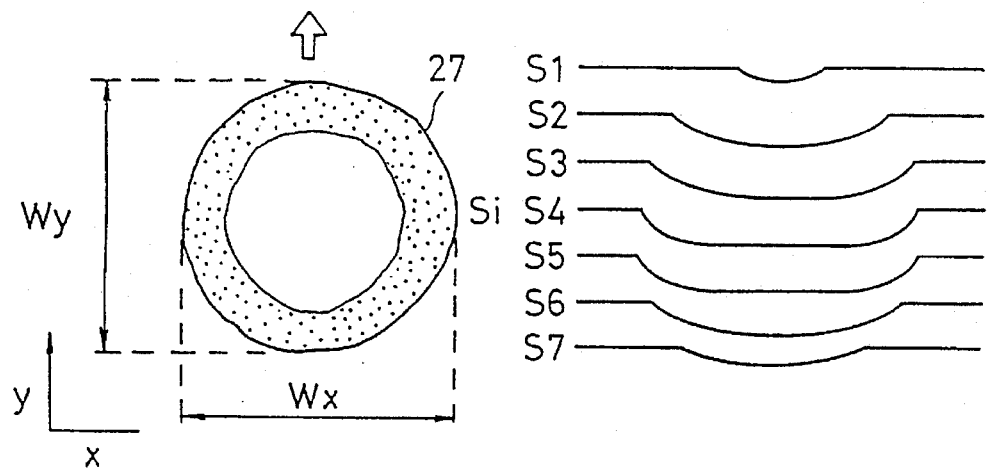
FIG. 4 is a view showing an example of an output signal from a line sensor camera.

As shown in FIG. 3, the particle detection area B in the sample flow 26 detected with the line sensor camera 32 is formed with the line sensor camera 32 in such a manner that primary(major) dimension extends across the flat sample flow 26 across its width. When particles 27a and 27b traverse this detection area B, light is prevented from reaching the line sensor camera 32 so that a signal Si as shown in FIG. 4 is output from the line sensor camera 32. Referring to FIG. 4, Symbol Wx designates a size of the particle in the direction of X whereas Wy a size of the particle in the direction of Y. Symbol i designates a scan number and Si a scan signal corresponding to a scan signal corresponding to the scan number i.

One particle is scanned more than once until it completely traverses the capturing area of the line sensor camera 32 which depends on the flow rate of the sample flow 26, the size of particles 27a and 27b and the scan cycle of the line sensor camera 32.

Subjecting the detection signal Si obtained at this time to binary value treatment or operation treatment provides in real time a detection signal D which represents the size of each particle with the pulse width. Incidentally, methods can be used which are described in Japanese Patent Application No. HEI 3-270106 and Japanese Patent Application No. HEI 3-270107.

The capturing operation with the above structure will be detailed hereinbelow.

The constant light-emitting lamp 14 constantly emits light. The light is rendered parallel with the collimator lens 16, reflected by the dichroic mirror 18, focused with the iris 20 and the condenser lens 22 and applied to the sample flow 26 with its focus on the detection area of the line sensor camera 32. The near-infrared ray that has transmitted this detection area B is reflected at the dichroic mirror 30 to form an image on the light receiving surface of the primary dimension camera inside the line sensor camera 32.

As described above, when the particle traverses the line sensor detection area B, the detection signal Si from the line sensor camera 32 changes so that the information on the size of the particle can be obtained in real time and the capturing magnification can be determined with respect to the particle.

When the particle is small as shown in FIG. 3 and it can be predicted that the particle passes through the capturing area A2 of high power, it is judged that the particle is captured at a high power. The flash lamp 10 is activated after waiting for the arrival of the particle into the high magnifying (power) capturing area (after several hundred μsec).

On the contrary, when the particle is large and it has been judged that the particle is to be captured at a low power, the flash lamp 10 is activated after waiting for the arrival of the particle into the low magnifying (power) capturing area A2 (after 0.5 to 1 msec).

Thus, when the particle traverses the detection area B of the line sensor camera 32, the size of the particle is immediately determined so that a judgment is made on whether or not the particle is to be captured at a low power or at a high power.

In this judgment, when the object particle is circular, the size of the particle is judged with the width Wx in the direction of X. When the object particle is not circular, the size of the particle is determined in consideration of the width Wy (the width in the traveling direction of the particle) in the direction of Y as well as the width Wx in the direction of X.

For example, suppose that Symbol "a" designates a reference for determining the size of the particle in the width Wx in the direction of X, and "b" a reference for determining the size thereof in the width Wy in the direction of Y. When both $Wx<a$ and $Wy<b$ are established, the particle is judged to be small so that the particle is captured at a high power. When either $Wx \geq a$ or $Wy \geq b$ is established, the size of the particle is determined to be large so that the particle is captured at a low power. In this case, it is possible to set both a and b to an equal value.

Incidentally, the width Wy in the direction of Y can be determined by multiplying the scanning times i of the same particle by the particle traveling distance in the scanning cycle period.

In this manner, the light-receiving system for capturing particles is divided into two systems, a high power projection system and a low power projection system. The capturing areas corresponding to each system are set to be different and the whole system is so designed that all particles can be finally captured with one video camera 50.

Light emitted by the flash lamp 10 is instantly applied to the capturing areas A1 and A2 of the video camera 50 so that the light is rendered parallel with the collimator lens 12, passing through the dichroic mirror 18. Then the light is focused with the condenser lens 22 and is applied to the capturing areas A1 and A2 of the video camera in the sample flow 26. The light that has passed through the sample flow 26 passes through the dichroic mirror 30 and is partially reflected with the half mirror 34 with the result that the reflected light forms an image on the position of the mask 36. On the other hand, the light that has passed through the half mirror 48 is entirely reflected on the mirror 42 to form an image on the position of the mask 44.

As shown in FIGS. 2(a) and 2(b), the masks 36 and 44 comprise openings (white blanks) which correspond to the respective capturing areas A1, A2 of the light receiving system. In other words, the mask 36 restricts the low power capturing area A1. Images formed on the area A1 are projected on the capturing surface (light receiving surface or image forming surface) on which CCD's of the video camera 50 are arranged after passing through the mirror 38 and a one time magnification relay lens followed by partially passing through the half mirror 48.

On the other hand, the mask 44 restricts the high power capturing area A2, and the image formed on the area A2 is further magnified four times with the four times magnification relay lens, thereby being reflected by the half mirror 48 and projected onto the capturing surface of the video camera 50.

When the reflection rates of the half mirrors 34 and 48 are set to one-fifth and four-fifths respectively, the brightness of each of the low-power and the high-power particle images which are four times different to each other in power can be made equal.

FIGS. 6(a) and 6(b) are views showing one example of the capturing screen captured with the video camera 50. Referring to FIG. 6(a), there is shown a high-power image which is captured at a timing of the high power, i.e., when small particles reach a high- power capturing area A2. FIG. 6(b) shows a low-power image at the low power which is captured at a timing of the low power, i.e., when large particles reach a low-power capturing area A1.

Figure 7:
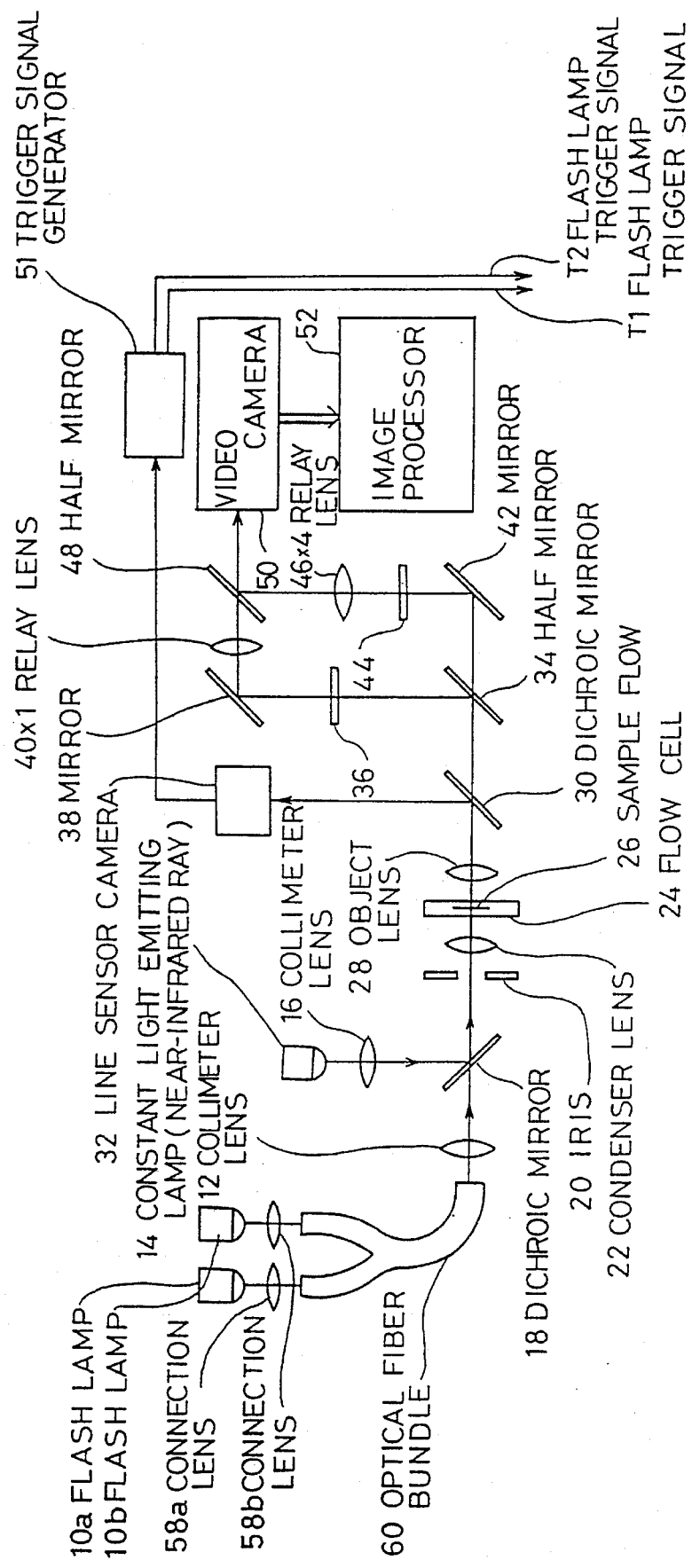
FIG. 7 is a view showing the imaging flow cytometer according to another embodiment of the present invention.

FIG. 7 is a view showing an imaging flow cytometer according to another embodiment of the present invention. In this particular embodiment, like reference numerals are given to constituents similar to the counterpart in the previous embodiment. Detailed description thereof is omitted.

In accordance with this particular embodiment, even when both small and large particles pass through a capturing area of the video camera 50 in a certain even number field period, the image flow cytometer of the present invention can capture both the low- power projection image of large particles and the high-power projection image of small particles within the same screen by using the fact that the capturing area of each of the two particles are remote from each other.

In other words, when a static image of particles that move within the flow cell 24 is captured with the flash lamp 10 as described in the above embodiment, normal frame accumulation type video camera is used to obtain a particle image having a high vertical resolution by a combination of an odd number field and an even number field.

Figure 8:
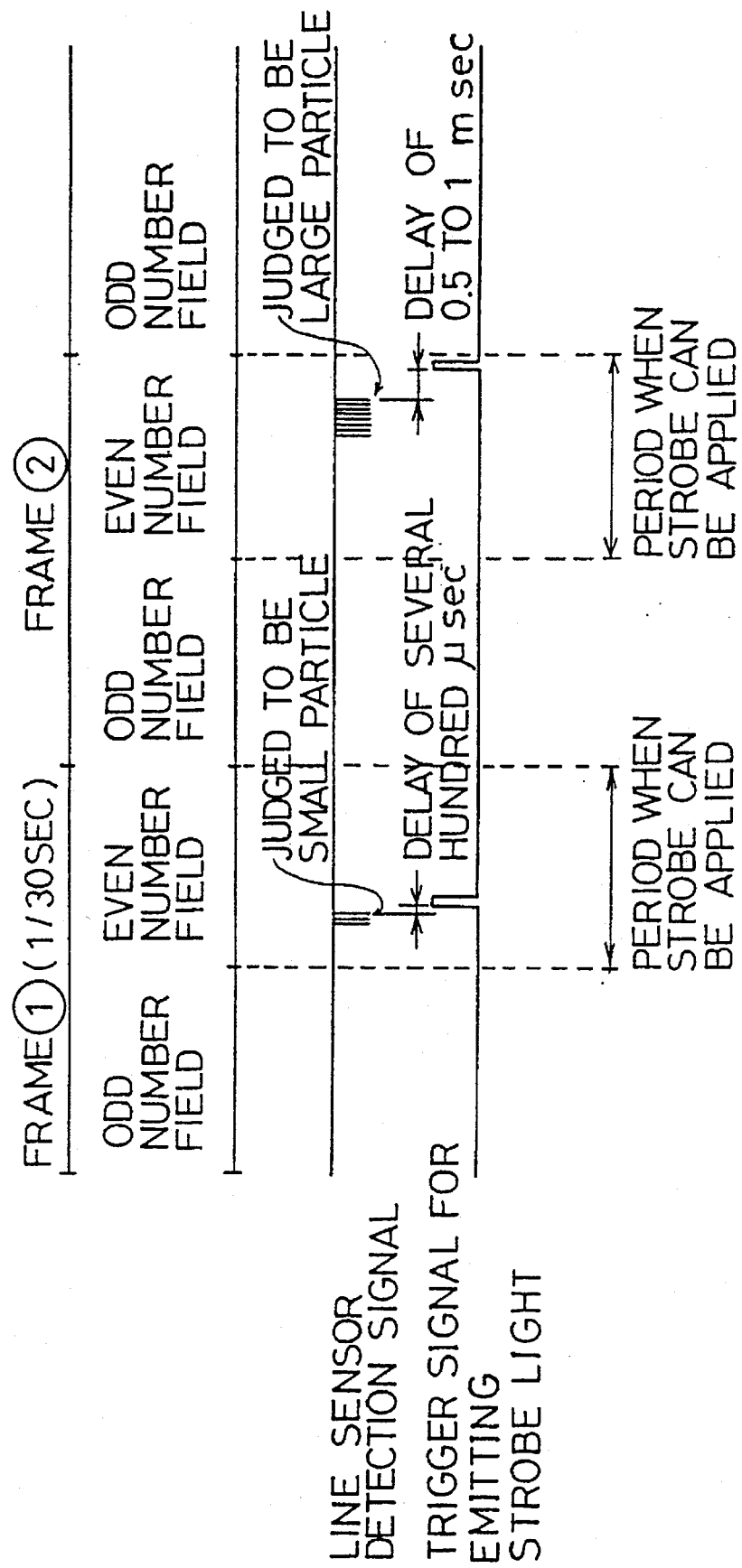
FIG. 8 is a view showing a irradiation timing in a flash lamp.

In such case, as shown in FIG. 8, the period in which the flash lamp 10 can be applied is restricted to the even number field period, particles that pass through the capturing area during the odd number field period cannot be captured (refer to Japanese Published Unexamined Patent Application No. HEI 4-72544 for further detail).

Besides, when two or more particles pass through the capturing area in a certain odd number field period, all the particles that pass through the area cannot be captured because multiple exposure must be avoided.

The embodiment has been made to improve this point. Even when small and large particles pass through the capturing area during a certain even number field period, both images of small and large particles can be captured.

Consequently, the present embodiment provides two flash lamps 10a and 10b, one for low-power capturing, and the other for high-power capturing as a flash lamp for capturing particle images. Then light applied by these flash lamps 10a and 10b is guided to an optical fiber bundle 60 comprising two fiber bundles 60a and 60b tied together at one end as shown in FIG. 9, followed by applying light to the sample flow 26 with the focus on each capturing area A1 and A2 as shown in FIG. 10.

In such structure, light applied to the low power capturing area A1 and light applied to the high power capturing area A2 are required to be distanced from each other or such light will be applied to the wrong capturing area. Otherwise, light applied from the optical fiber bundle 60 is required to be approximated to the critical illumination as much as possible. Then double exposure should be prevented as much as possible on the light receiving surface of the video camera 50.

The structure of the light receiving system for monitoring particles that pass through the capturing area and for capturing particles are the same as the above embodiment.

Figure 11A:
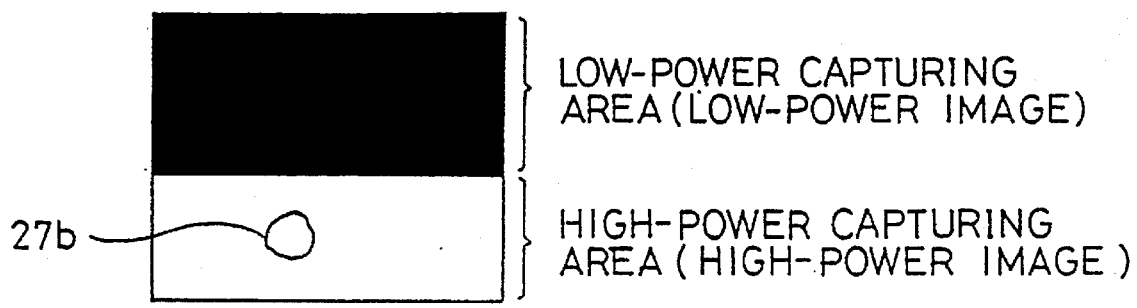
FIGS. 11(a)–11(c) are views showing examples of a capturing screen in another embodiment.
Figure 11B:
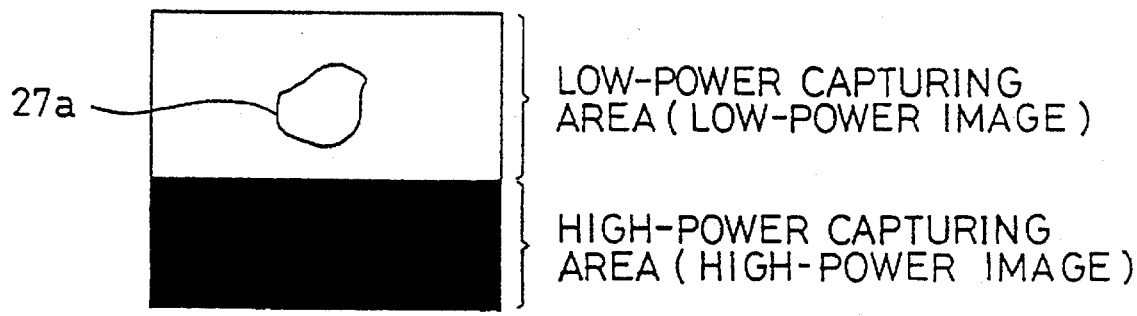
Figure 11C:
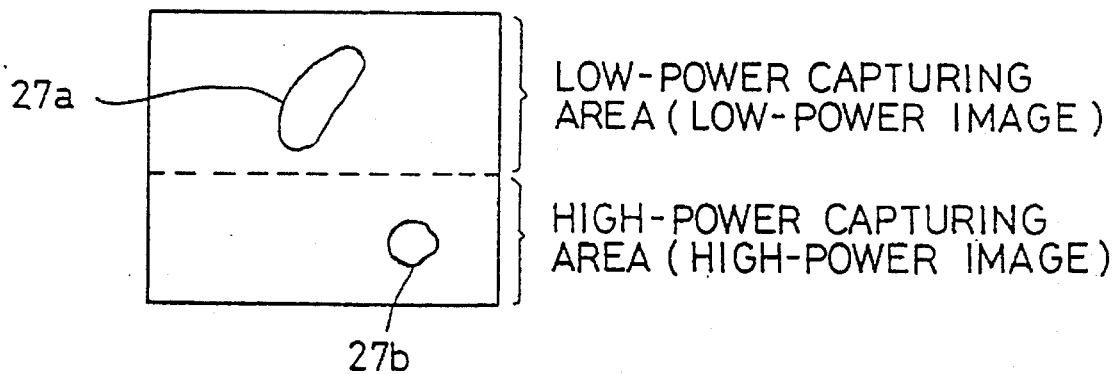
Figure 12:
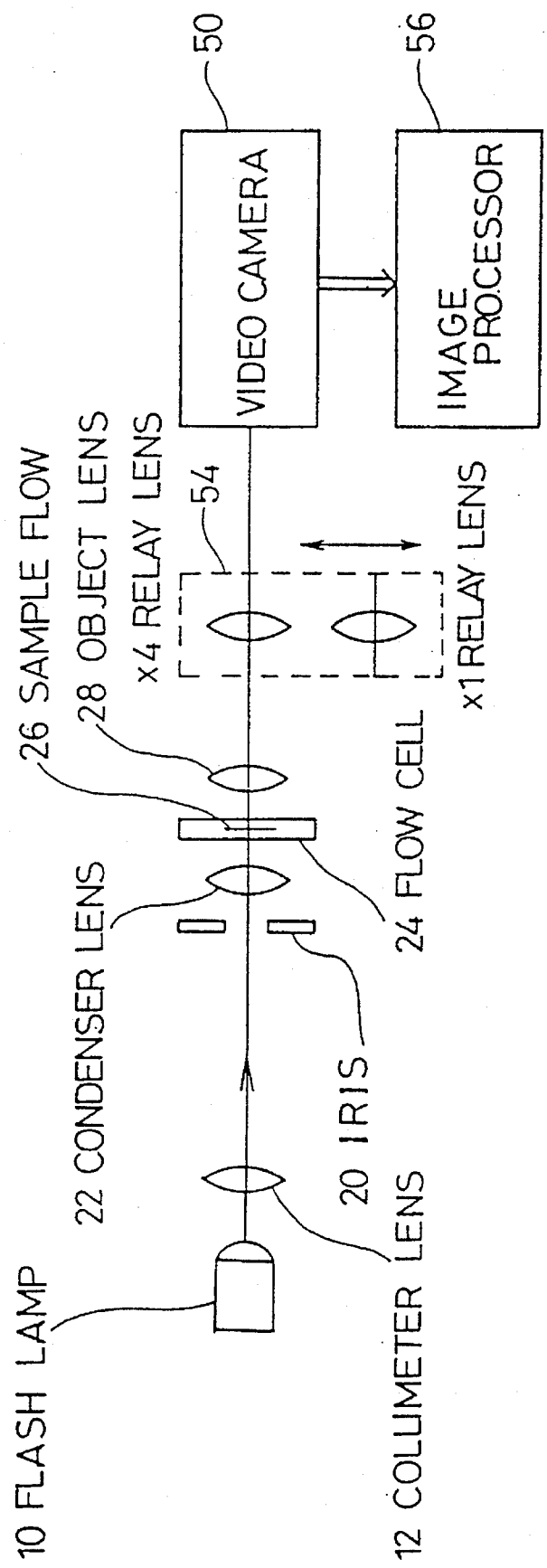
FIG. 12 is a view showing an outline of a conventional imaging flow cytometer.

FIGS. 11(a)–11(c) show one example of the capturing screen in this embodiment. Referring to FIG. 11(a), there is shown an example of a capturing screen that is obtained when only a small particle 27b passes through the high power capturing area A2 in a certain even number field period, FIG. 11 (b) is an example of a capturing screen obtained when only a large particle passes through the low-power capturing area A1 in a certain even number field period, and FIG. 11(c) is an example of a capturing screen obtained when the large particle 27a and the small particle 27b pass through the low and high-power capturing areas A1 and A2 respectively.

In accordance with the present invention, image light obtained from the subject particles is divided so that respective images of the subject particles can be magnified at different magnifications and selectively captured. Consequently, particles can be efficiently captured by instantly switching the magnification depending on the size thereof in one measurement sequence.

When a particle detector is provided, then a subject particle can be captured after the flow cytometer confirms that the particle passes through the capturing area of the video camera. Thus, a particle image magnified at a power corresponding to the size of the particle can be obtained in one measurement sequence. The measurement time can be shortened, the substantial amount of the sample that can be analyzed largely increases and a highly reproducible measurement result can be obtained.

When the capturing area of the video camera is divided into at least two divided capturing areas along the direction of the flow of the subject particles so as to be given as a low-power capturing area and a high-power capturing area, both small particles magnified at a high power and large particles magnified at a low power can be obtained in one capturing screen thereby increasing the number of particles that can be captured per unit time.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An imaging flow cytometer comprising:

flow means having a transparent passage through which subject particles move in a separate fluidity, the subject particles being present in a sample liquid;

irradiation means for irradiating a sample liquid flow which flows in the transparent passage with light;

beam splitting means for distributing light incident thereon from each of the particles that are present in the sample liquid flow irradiated with the light simultaneously to at least two optical paths;

capturing means which has a light receiving surface on which an image is formed;

projecting means for respectively magnifying the light distributed along the at least two optical paths by said beam splitting means with respectively different magnification powers and forming an image on respective portions of the light receiving surface of said capturing means; and image processing means for storing and displaying images of particles captured by said capturing means.

2. The imaging flow cytometer according to claim 1, wherein said capturing means comprises one video camera wherein the light receiving surface is projected to the transparent passage to form two capturing areas defined on the sample liquid flow, one of said capturing areas being for a high power magnification and an other of said capturing areas being for a low power magnification, whereby light from particles in each of said capturing areas is projected by said projecting means to form an image on each portion of the light receiving surface of said video camera.

3. The imaging flow cytometer according to claim 2, further comprising:

auxiliary irradiation means for irradiating the sample liquid flow with light at a location upstream of an area irradiated by said irradiation means;

particle detection means for detecting a size of particles that are present in the sample liquid flow by detecting the liquid from the particle irradiated by said auxiliary irradiation means; and control means for irradiating the sample liquid flow by said irradiation means when a detected subject particle reaches the capturing area corresponding to the size of the detected subject particle so that an image of each of the detected subject particles is captured at the magnification power corresponding to the size of the detected subject particle.

4. The imaging flow cytometer according to claim 3, wherein said particle detection means comprises an image sensor having a light receiving surface having a major dimension and a capturing area that extend in a direction perpendicular to the flow of subject particles.

5. The imaging flow cytometer according to claim 3, wherein said irradiation means comprises:

light sources equal in number to the number of capturing areas; and light guiding means for directing light coming from each of said light sources to respective capturing areas so that subject particle images in each of the capturing areas are formed on respective portions of the light receiving surface of said video camera depending on the light coming from each of said light sources.

6. The imaging flow cytometer according to claim 5, wherein said light guiding means comprises a branched optical fiber bundle.

7. An imaging flow cytometer comprising:

flow means having a transparent passage through which subject particles move in a separate fluidity, the subject particles being present in a sample liquid;

irradiation means for irradiating a sample liquid flow which flows in the transparent passage with light;

beam splitting means for distributing light incident thereon from the subject particles irradiated with the light from said irradiation means in the sample liquid flow simultaneously to both of first and second optical paths having different first and second magnification powers;

capturing means, having a light receiving surface, for generating image signals representative of light from the subject particles incident upon the light receiving surface from the first and second optical paths; and image processing means, coupled to said capturing means, for storing the image signals and displaying images of the subject particles from the image signals generated by said capturing means.

8. The imaging flow cytometer of claim 7, wherein the light from the first and second optical paths are incident upon respectively different first and second portions of the light receiving surface of said capturing means.

9. The imaging flow cytometer of claim 8, wherein said capturing means comprising a video camera wherein the light receiving surface is projected to the transparent passage of said flow means to form first and second capturing areas corresponding to higher and lower magnification powers, respectively.

10. The imaging flow cytometer of claim 9, wherein light from subject particles of the first capturing area are magnified along the first optical path to be incident on the first portion of the light receiving surface of said capturing means and light from subject particles of the second capturing area are magnified along the second optical path to be incident on the second portion of the light receiving portion of said capturing means.

11. The imaging flow cytometer of claim 7 wherein the light receiving surface of said capturing means has first and second light receiving portions corresponding to light from the first and second optical paths respectively, the imaging flow cytometer further comprising:

auxiliary irradiation means for irradiating the sample liquid flow with light at a location upstream of an area irradiated by said irradiation means;

particle detection means for detecting a size of subject particles present in the sample liquid flow by detecting the light from subject particles irradiated by said auxiliary irradiation means; and control means for directing said irradiation means to irradiate the sample liquid flow when a detected subject particle reaches either of a first or second capturing area in the transparent passage of said flow means corresponding to the size of the detected subject particle, wherein light from subject particles of a smaller size irradiated in the first capturing area is magnified along the first optical path and light from subject particles of a larger size irradiated in the second capturing area is magnified along the second optical path.

12. The imaging flow cytometer of claim 11, wherein said irradiation means comprises first and second irradiators for respectively irradiating the first and second capturing areas in the transparent passage of said flow means.

13. The imaging flow cytometer of claim 12, wherein said first and second irradiators simultaneously irradiate the first and second capturing areas in the transparent passage of said flow means to enable simultaneous display of image signals corresponding to subject particles of smaller size generated by the first light receiving portion of said capturing means and image signals corresponding to subject particles of larger size generated by the second light receiving portion of said capturing means.

14. The imaging flow cytometer of claim 11, wherein said auxiliary irradiation means irradiates infrared light.

15. The imaging flow cytometer of claim 11, wherein said particle detection means comprises an image sensor having a light receiving surface having a major dimension and capturing area which extend in a direction perpendicular to the flow of subject particles.

16. A method of imaging subject particles in an imaging flow cytometer having flow means with a transparent passage through with the subject particles move in separate fluidity in a sample liquid, the method comprising:

(a) irradiating the sample liquid flow which flows through the transparent passage with light;

(b) distributing light from the subject particles irradiated during said step (a) simultaneously to first and second optical paths having different first and second magnification powers;

(c) capturing light from the first and second optical paths on a light receiving surface of capturing means to generate image signals representative of light from the subject particles; and (d) processing the image signals generated in said step (c) to display images of the subject particles.

17. The method of imaging subject particles of claim 16, wherein said step (c) comprises light from the first and second optical paths using respective different first and second portions of the light receiving surface of the capturing means.

18. The method of imaging subject particles of claim 17, wherein said step (c) comprises projecting the first and second portions of the light receiving surface of the capturing means to the transparent passage of the flow means to form first and second capturing areas in the sample liquid flow corresponding to higher and lower magnification powers, respectively.

19. The method of imaging subject particles of claim 18, wherein said step (b) comprises magnifying light from subject particles of the first capturing area along the first optical path to be incident on the first portion of the light receiving surface of the capturing means and magnifying light from subject particles of the second capturing area along the second optical path to be incident on the second portion of the light receiving surface of the capturing means.

20. The method of imaging subject particles of claim 16, wherein the light receiving surface of the capturing means has first and second portions for receiving light from the first and second optical paths, the method further comprising:

(e) irradiating the sample liquid flow with light at a location upstream of an area irradiated during said step (a);

(f) detecting a size of subject particles present in the sample liquid flow by detecting the light from subject particles irradiated during said step (e); and (g) directing irradiation of the sample liquid flow in said step (a) when a detected subject particle reaches either of a first or second capturing area in the transparent passage of the flow means corresponding to the size of the detected subject particle, wherein light from subject particles of a smaller size irradiated in said step (a) in the first capturing area is magnified along the first optical path and light from subject paths of larger size irradiated in said step (a) in the second capturing area is magnified along the second optical path.

21. The method of imaging subject particles of claim 20, wherein said step (a) comprises respectively irradiating the first and second capturing areas in the transparent passage of the flow means with first and second irradiators.

22. The method of imaging subject particles of claim 21, wherein said step (a) comprises simultaneously irradiating the first and second capturing area in the transparent passage of the flow means respectively with the first and second irradiators to enable simultaneous display in said step (d) of image signals corresponding to subject particles of smaller size generated by the first portion of the light receiving surface of the capturing means and image signals corresponding to the subject particles of larger size generated by the second portion of the light receiving surface of the capturing means.

23. The method of imaging subject particles of claim 20, wherein said step (e) comprises irradiating the sample liquid flow with infrared light.

* * * * *